United States Patent [19]
Schrier

[11] Patent Number: 5,750,111
[45] Date of Patent: May 12, 1998

[54] MILD NEWCASTLE DISEASE VIRUS VACCINE

[75] Inventor: Carla Christina Schrier, Boxmeer, Netherlands

[73] Assignee: Akzo Nobel N.V., Arnhem, Netherlands

[21] Appl. No.: 781,436

[22] Filed: Jan. 10, 1997

Related U.S. Application Data

[63] Continuation of Ser. No. 509,914, Aug. 1, 1995, abandoned.

[51] Int. Cl.$^6$ .................... A61K 39/17; C12N 7/00; C12N 7/04
[52] U.S. Cl. .................... 424/214.1; 435/69.3; 435/236; 435/240.2
[58] Field of Search .................... 424/214.1; 435/69.3, 435/236, 240.2

[56] References Cited

U.S. PATENT DOCUMENTS

| | | | |
|---|---|---|---|
| 2,767,117 | 10/1956 | Crawley | 435/235.1 |
| 4,053,583 | 10/1977 | Gits et al. | 424/90 |
| 4,235,876 | 11/1980 | Gits et al. | 424/89 |
| 4,279,893 | 7/1981 | Kreimer et al. | 424/89 |
| 5,118,502 | 6/1992 | Glisson et al. | 424/89 |
| 5,149,530 | 9/1992 | van Wiltenburg | 424/89 |
| 5,250,298 | 10/1993 | Gelb, Jr. | 424/89 |
| 5,427,791 | 6/1995 | Ahmad et al. | 424/214.1 |

FOREIGN PATENT DOCUMENTS

| | | |
|---|---|---|
| 0 351 908 | 1/1990 | European Pat. Off. . |
| 2062461 | 5/1981 | United Kingdom . |
| WO 90 06131 | 6/1990 | WIPO . |
| WO 90 15623 | 12/1990 | WIPO . |

OTHER PUBLICATIONS

D.J. Alexander, *Diseases in Poultry*, 9th Ed., Chapter 19, "Newcastle Disease and Other Paramyxovirus Infections," pp. 496–519, B.W. Calnek (Ed.), Wolfe Publishing Ltd., Ames Iowa, USA.

Spradbrow et al., "Serological Response of Chickens to Oral Vaccination with Newcastle Disease Virus," Veterinary Microbiology vol. 16:255–262, 1988.

Shukla et al., "Vaccination with CDF–66 Strain of Newcastle Disease Virus," Trop. Anim. Hlth. Prod. vol. 14:15–19, 1982.

Srinivasappa et al. Avian Diseases. vol. 30, No. 3 pp. 562–567, 1986.

Palmieri, S. Avian Diseases. vol. 33, No. 2 pp. 351–356.

*Primary Examiner*—Ponnathapura Achutamurthy
*Assistant Examiner*—Phuong T. Bui
*Attorney, Agent, or Firm*—William M. Blackstone; Mary E. Gormley

[57] ABSTRACT

The present invention provides the novel Newcastle disease virus strain C2 which is able to induce a solid immune response in poultry without adverse vaccination reactions.

9 Claims, No Drawings

MILD NEWCASTLE DISEASE VIRUS VACCINE

This is a continuation of application Ser. No. 08/509,914 filed Aug. 1, 1995, now abandoned.

The present invention is concerned with a mild Newcastle disease virus (NDV) strain and a vaccine for use in the protection of poultry against Newcastle disease comprising said NDV strain.

Newcastle disease is a viral infection of poultry with a wide geographical distribution causing great economical losses in the poultry industry. Newcastle disease virus (NDV) is the etiologic agent of this disease and represents the prototype virus of the genus Paramyxovirus. Newcastle disease is complicated in that different isolates and strains of the virus may induce enormous variation in the severity of the disease. In general, the younger the chicken the more acute and severe the disease. The infection may take place by either inhalation or ingestion and the infectious form of the virus is spread from one bird to another.

As mentioned-above several pathotypes of NDV have been identified, i.e. velogenic, mesogenic and lentogenic. Although these terms result from laboratory tests carried out both in vivo and in vitro, the terms are now generally used to describe viruses of low, moderate or high virulence for chickens. The neurotropic velogenic form of disease is caused by highly pathogenic strains of NDV and is characterised by a sudden onset of severe respiratory signs followed by neurological signs. In most cases the infected animals do not survive. Viscerotropic velogenic NDV strains are highly pathogenic and cause high mortality and severe lesions in the gastro-intestinal tract. Mesogenic strains of NDV usually cause severe respiratory disease in fully susceptible birds, and in adult birds cause a marked drop in egg production. Lentogenic strains of ND virus cause generally a mild disease which is characterised by respiratory signs, especially in young fully susceptible birds.

In order to reduce the economic losses due to ND in the commercial poultry industry chickens have been vaccinated against ND. Live vaccines derived from lentogenic and mesogenic strains have been applied routinely, the mesogenic vaccine being suitable only for secondary vaccination. However, also in the lentogenic group there is a considerable range in virulence. NDV strains used as live vaccines include V4, Hitchner B 1, F, La Sota (lentogenic), and strain H, Mukteswar, Koinarov and Roakin (mesogenic). The main advantage of live ND vaccines is that these can be administered by inexpensive mass application techniques, such as spray and drinking water application. However, live vaccines may cause severe vaccination reactions, in particular in the respiratory tract after spray vaccination. Because of this, it is important to use extremely mild virus for vaccination, in particular for primary vaccination, however, as a result, multiple applications of vaccines are usually needed.

Inactivated vaccines are administered by injection, generally to older birds. Mostly, these vaccines contain the killed virus mixed with an adjuvant carrier, such as aluminium hydroxide or a water-in-oil emulsion. Viruses used for the preparation of oil-emulsion vaccines include Ulster 2C, Hitchner B1, La Sota, Roakin and various virulent viruses (D. J. Alexander, In Diseases of Poultry, 9th edition 1991, eds. Calnek et al., Iowa State University Press, Ames, Iowa, 496–519).

Because the commonly used live NDV strains Hitchner B1 and La Sota still cause moderate respiratory vaccination reactions a need exists for even more mild NDV vaccine strains causing no (respiratory) vaccination reactions in inoculated animals, yet produce a solid immunity against the disease. Several of such strains have been described in the prior art. U.S. Pat. No. 5,250,298 (University of Delaware) discloses a live, cold-adapted temperature-sensitive mutant of the Hitchner B1 parent strain, designated CaTs. U.S. Pat. No. 5,149,530 (Duphar Int. Res. B.V.) describes the strain NDW derived from the Ulster 2C strain. Furthermore, in U.S. Pat. No. 5,188,502 (University of Georgia Research Foundation, Inc.) a naturally attenuated NDV strain isolated from the intestinal tract of a turkey showing no signs of respiratory disease is disclosed.

According to one aspect of the invention there is provided a novel NDV strain designated C2, which is deposited at the CNCM of the Institute Pasteur, 25 Rue du Docteur Roux, Paris, France, under accession No. I-1614 on Jul. 26, 1995. The virus strain according to the invention is distinct from the existing NDV (vaccine) strains and causes no vaccination reactions, neither in the respiratory tract nor in other organs, yet is able to induce a solid immune response.

The experiment described in Example 1 illustrate the differences between the claimed NDV strain and existing NDV vaccine strains in addition to the favourable vaccination properties of the claimed NDV strain.

Another aspect of this invention is a vaccine for use in the protection of poultry against ND comprising viruses of the novel NDV C2 strain mentioned-above, together with a pharmaceutical acceptable carrier or diluent.

The viruses of the NDV C2 strain can be incorporated into the vaccine as live or inactivated viruses.

The viruses of the NDV C2 strain comprise viruses derived from the deposited viruses as well as those progeny viruses derived from the deposited NDV C2 strain by serial passaging, for example in embryonated eggs or in a cell culture.

NDV viruses of the C2 strain to be incorporated in a vaccine according to the invention can be obtained by conventional methods. Briefly, a susceptible substrate is inoculated with NDV C2 viruses and propagated until the virus replicated to a desired titer after which NDV containing material is harvested.

Every substrate which is able to support the replication of ND viruses can be used in the present invention, including primary (avian) cell cultures, such as chicken embryo fibroblast cells (CEF) or chicken kidney cells (CK), or mammalian cell lines such as the VERO cell line or baby hamster kidney (BHK) cell line.

Preferably, the NDV C2 viruses are propagated in embryonated chicken eggs.

In particular, the substrate on which these ND viruses are propagated are SPF embryonated eggs. Embryonated eggs can be inoculated with, for example 0.2 ml NDV containing allantoic fluid comprising at least $10^{2.0}$ EID$_{50}$ per egg. Preferably, 9–12 day-old embryonated eggs are inoculated with about $10^{5.0}$ EID$_{50}$ and subsequently incubated at 37° C. for 2–4 days. After 2–4 days the ND virus product can be harvested preferably by collecting the allantoic fluid. The fluid can be centrifuged thereafter for 10 min. at 2500 g followed by filtering the supernatant through a filter (100 µm).

The vaccine according to the invention containing the live virus can be prepared and marketed in the form of a suspension or in a lyophilised form and additionally contains a pharmaceutically acceptable carrier or diluent customary used for such compositions. Carriers include stabilisers, preservatives and buffers. Suitable stabilisers are, for example SPGA, carbohydrates (such as sorbitol, mannitol, starch, sucrose, dextran, glutamate or glucose), proteins (such as dried milk serum, albumin or casein) or degradation products thereof Suitable buffers are for example alkali metal phosphates. Suitable preservatives are thimerosal, merthiolate and gentamicin. Diluents include water, aqueous buffer (such as buffered saline) and polyols (such as glycerol).

If desired, the live vaccines according to the invention may contain an adjuvant.

Although injection of the live vaccine according to the present invention is possible, the vaccine is preferably administered by the inexpensive mass application techniques commonly used for ND vaccination. These techniques include drinking water and spray vaccination. Because of the extremely mild properties of the present vaccine virus, spray administration of the vaccine is in particular contemplated.

In the administration by the drinking water route it is customary to deprive the animals of water for about 2 to 4 hours before placing the vaccine containing water in front of them, and it is important that there is enough drinker space for all birds to drink evenly. The vaccine is applied in fresh drinking water at a concentration calculated to give each bird a sufficient dose.

In order to prevent a dramatic reduction of the viable vaccine virus by the presence of small amounts of chlorine, iron, zinc or copper ions in the drinking water, preferably a protectant such as skim milk (powder) is added to the water containing vaccine.

The spray method, comprising the coarse spray and aerosol administration, involves the administration of the live ND virus vaccine incorporated in small liquid particles. In the coarse spray method particles usually have an initial droplet size ranging from 10 to 100 microns and in the aerosol administration method droplets usually range from <1 to 50 microns.

In order to prevent inactivation of the live vaccine virus because of increased concentration of dissolved salts as a result of desiccation of the (tap) water particles, small amounts of a protein protectant, such as skimmed milk, skimmed milk powder or gelatin can be added to aqueous phase.

For the generation of the small particles, conventional spray-apparatus and aerosol generators can be used, such as the commercially available spray generators for knapsack spray, hatchery spray and atomist spray. Also the drinking water vaccination can be carried out using conventional apparatus. Details concerning conventional spray/aerosol- and drinking water vaccination can be found in the "Compendium, administration of poultry vaccines" issued by the Gezondheidsdienst voor Pluimvee, Doorn, The Netherlands, van Eck et al., VI–VII, 1988.

Alternative methods for the administration of the live vaccine include eye drop and beak dipping administration.

In another aspect of the present invention a vaccine is provided comprising the ND viruses of the C2 strain in an inactivated form. The major advantage of an inactivated vaccine is the extremely high levels of protective antibodies of long duration that can be achieved.

The aim of inactivation of the ND viruses harvested after the propagation step is to eliminate reproduction of the viruses. In general, this can be achieved by chemical or physical means. Chemical inactivation can be effected by treating the viruses with, for example, enzymes, formaldehyde, β-propiolactone, ethylene-imine or a derivative thereof. If necessary, the inactivating compound is neutralised afterwards. Material inactivated with formaldehyde can, for example, be neutralised with thiosulphate or sodium metabisulfite. Physical inactivation can preferably be carried out by subjecting the viruses to energy-rich radiation, such as UV light, X-radiation or γ-radiation. If desired, the pH can be brought back to a value of about 7 after treatment.

A vaccine containing the inactivated ND viruses can, for example comprise one or more of the above-mentioned pharmaceutically acceptable carriers or diluents suited for this purpose.

Preferably, an inactivated vaccine according to the invention comprises one or more compounds with adjuvant activity. Suitable compounds or compositions for this purpose include aluminium hydroxide, -phosphate or -oxide, oil-in-water or water-in-oil emulsion based on, for example a mineral oil, such as Bayol F® or Marcol 52® or a vegetable oil such as vitamin E acetate, and saponins.

The vaccine according to the invention comprises an effective dosage of the NDV C2 viruses as the active component, i.e. an amount of immunising NDV material that will induce immunity in the vaccinated birds against challenge by a virulent ND virus. Immunity is defined herein as the induction of a significant higher level of protection in a population of birds after vaccination compared to an unvaccinated group.

Typically, the live vaccine according to the invention can be administered in a dose of $10^{3.0}$–$10^{8.0}$ embryo infectious dose$_{50}$ (EID$_{50}$) per animal, preferably in a dose ranging from $10^{5.0}$–$10^{7.0}$ EID$_{50}$.

Inactivated vaccines may contain the antigenic equivalent of $10^{4.0}$–$10^{9.0}$ EID$_{50}$ per animal, preferably between $10^{6.0}$–$10^{8.0}$ EID$_{50}$ per animal.

Inactivated vaccines are administered parenterally, e.g. intramuscularly or subcutaneously.

Although, the vaccine according to the present invention may be used effectively in chickens, also other poultry such as turkeys, guinea fowl and partridges may be successfully vaccinated with the vaccine. Chickens include broilers, reproduction stock and laying stock.

Because of the mild character of the NDV C2 virus the vaccine according to the present invention can be administered to the birds directly after hatch, i.e. from one-day-old on. The vaccine can be used as a primary vaccination, if desired followed by one or more secondary vaccinations (booster vaccination) with the same or different NDV vaccine. To obtain the desired level of protection without serious vaccination reactions, the vaccine according to the invention is particularly suited for incorporation in vaccination programmes that involve the sequential use of progressively more virulent viruses, such as Clone 30®, La Sota, Hitchner B1, or programmes that start with the administration of a mild live virus vaccine followed by the administration of an inactivated vaccine.

As an example broilers may be vaccinated at one-day-old followed by a secondary immunization at 14–21 days. Laying stock or reproduction stock may be vaccinated at 1–10 days followed by booster vaccinations on 26–38 days and 10–12 weeks.

The invention also includes combination vaccines comprising, in addition to the viruses of the NDV C2 strain, a vaccine comprising one or more immunogens derived from other pathogens infectious to poultry.

Preferably, the combination vaccine additionally comprises one or more vaccine strains of infectious bronchitis virus (IBV), infectious bursal disease virus (IBDV), chicken anemia agent (CAA) or reovirus.

A comprehensive description of all aspects of ND vaccination and vaccine production is disclosed by Allan et al., FAO Animal Production and Health Series No. 10, FAO, Rome, 1978; Cross G.M, In D.J. Alexander (ed.), Newcastle Disease, 333–346, Kluwer Acad. Public., Boston, 1988 and Meulemans, In. D.J. Alexander (ed.) Supra, 318–332.

EXAMPLE 1

Safety of NDV C2 vaccine 1.1. Comparisons with respect to respiratory reactions to the lentogenic NDV strains Hitchner B1 and C2 were made under standardised conditions (van Eck, J.H.H. et al., Avian Pathology 20, 497–507, 1991) based on body weight gain, mortality rate and susceptibility to colibacillosis following aerosol application of the vaccine and subsequent intratracheal inoculation of virulent E. coli bacilli (strain 506; O780K80).

Experimental design

Respiratory reaction in SPF-WL hens to the NDV Hitchner B 1 strain was compared with the respiratory reaction to the NDV C2 strain.

Day 0: Hatch of chicks: SPF-WL chicks (Intervet, Boxmeer). In the experiment only hens were used.

Day 1: Birds were weighed individually. Three groups, of which the average body weights did not differ significantly, were formed. Each group consisted of 30–34 chickens. Group size, corrected for non-specific mortality is presented in Table 1. Two groups of chickens were exposed to a standardised aerosol of one of the NDV strains, while the third group received an aerosol of peptone (placebo group). Immediately after aerosol exposure, groups were housed separately in similar negative pressure isolators.

Day 8: Surviving birds were weighed individually. Subsequently all chickens were intratracheally inoculated with virulent E. coli bacteria.

Day 15: Again surviving chicks of all groups were weighed individually, necropsied and colibacillosis lesions were scored.

Chickens were inspected daily and macroscopical examination was performed on all dead chicks. Special attention was given to the respiratory tract and to colibacillosis lesions. Colibacillosis lesions were scored in the following organs: thoracic airsac, pericardium and liver. The maximum score per bird was 12. Mean lesion scores per group were calculated.

Vaccinal reaction index (VRI) is based on weight loss due to vaccination. VRI ranges from 0 to 10. VRI's were calculated covering the periods of day 1 to 8 (VRI 1) and day 1 to 15 (VRI 2). VRI 1 reflects the growth depressing and mortality inducing potency of the vaccine, while VRI 2 moreover reflects the potency to increase susceptibility to colibacillosis.

RESULTS

Clinical inspection

Chickens in the peptone group did not show clinical signs of disease, nor did birds of the NDV C2 vaccinated group during the first 8 days of the experiment. In birds exposed to the NDV Hitchner B1 vaccine, from two or three days following exposure an extremely severe respiratory reaction was observed. All birds exhibiting open-mouth breathing changing in snapping at breath with stretched neck.

From two days after E.coli inoculation pumping breathing was observed in the surviving birds vaccinated with NDV Hitchner B 1. In the group exposed to the NDV C2 strain only a few birds showed mild respiratory signs after E. coli inoculation.

Mortality, body weight and lesion score

Specific mortality, body weight and lesion score are presented in Table 1. In the group vaccinated with the Hitchner B1 strain 63% of the birds died during the first 8 days after aerosol exposure and 91% of the remaining birds died after intratracheal inoculation with E. coli, while none of the birds in the NDV C2 strain inoculated group and the peptone group died.

In the group vaccinated with the NDV Hitchner B1 vaccine strain negative effects were observed on body weight both at 8 and 15 days of age and on mean lesion score and percentage of chickens with colibacillosis lesions, although at 15 days of age only the values of one surviving chicken could be determined.

The NDV C2 vaccination had no/hardly any effect on either body weight gain at 8 or at 15 days of age or the incidence and severity of colibacillosis lesions.

Vaccinal reaction index

VR indices are presented in Table 2. In the with the NDV C2 vaccinated groups both VRI 1 and the VRI 2 were very low.

On the other hand the VRI 1 and VRI 2 of the NDV Hitchner B1 vaccinated group were extremely high.

The NDV C2 strain is safe with respect to respiratory reaction. Even in chickens, in which the NDV Hitchner B1 strain caused severe respiratory distress and a high susceptibility to colibacillosis, the NDV C2 strain hardly induced any adverse reaction at all.

TABLE 1

Vaccinal reaction and seroresponse of SPF-WL hens exposed to aerosols[1] of live Newcastle Disease Virus strains at day-old and inoculated intra-tracheally with E. coli strain 506[2] at 8 days of age.

| | | | Age (days) | | | | | 15 | | |
|---|---|---|---|---|---|---|---|---|---|---|
| | | | 1 | 1–8 | 8 | 9–15 | | | Colibacillosis[4] | |
| Vaccine | Virus titre of aerosol ($\log_{10}$/m³) | Number of chicks | Mean weight ± s.d.[3] (g) | Mortality | Mean weight ± s.d.[3] (g) | Mortality | Mean weight ± s.d.[3] (g) | Mean lesion score | Number of affected chickens (%) | Mean HI ND titre[5] ± s.d. |
| C2 strain | 8.8 | 34 | 32 ± 3 | 0 | 68 ± 5 | 0 | 123 ± 10 | 0.7 | 12 (35) | 7.0 ± 0.7 |
| Hitchner B1 | 8.7 | 30 | 32 ± 3 | 19 | 37 ± 8 | 10 | 73 ± 0[7] | 7.0[7] | 1 (100)[7] | 10.0 ± 0.07[7] |
| Peptone[6] | — | 30 | 32 ± 3 | 0 | 70 ± 8 | 0 | 130 ± 14 | 0.0 | 0 (0) | 4.0 ± 0.0 |

[1] = exposure time = 30 minutes
[2] = E. coli dose: 10⁴ bacilli in 0.2 ml phosphate buffered saline per chicken
[3] = s.d. = standard deviation
[4] = colibacillosis lesions refer to live chickens
[5] = mean $\log_2$ haemagglutination inhibition titre to Newcastle Disease virus
[6] = placebo group: exposed to an aerosol of peptone at day-old and inoculated intratracheally with E. coli strain 506 at 8 days of age
[7] = value of only one chicken

TABLE 2

Vaccination reaction indices of Newcastle Disease vaccine.

| Vaccine | VRI 1 | VRI 2 |
|---|---|---|
| C2 strain | 0.3 | 0.5 |
| Hitchner B1 | 8.1 | 9.8 |

EXAMPLE 2

Virus identification 2.1: Elution time

The ability of NDV to agglutinate red blood cells (RBCs) is due to the binding of the HN protein to receptors on the surface of the RBCs. The enzyme neuraminidase is also part of the HN molecule and present in all members of the Paramyxovirus genus. An obvious consequence of the possession of this enzyme is the gradual elution of agglutinated RBCs. The rate of elution of chicken RBCs agglutinated by NDV has been used as a method of broadly grouping NDV isolates as rapid or slow eluters (Spalatin, J. et al., Avian Diseases 14, 542–549, 1970).

The rate of elution of chickens RBCs agglutinated by either the NDV Hitchner B1 strain, the NDV C2 strain, the NDW strain or the CaTs strain has been determined. The following results were obtained:

TABLE 3

RBC elution

| Virus | Elution rate (hours |
|---|---|
| Hitchner B1 | <7 rapid eluter |
| CaTs | <7 rapid eluter |
| NDW | >24 slow eluter |
| C2 | >24 slow eluter |

2.2: Reaction with monoclonal antibody AVS 1

Monoclonal antibodies are directed against usually very small areas (termed epitopes) on an antigen and are thus highly specific. This specificity can be employed to show similarities or differences between viruses based on their ability to react with these antibodies.

The reactivity of one well-characterized NDV monoclonal antibody AVS-1 and several NDV strains was evaluated using the hemagglutination-inhibition (HI) test.

The HI test was carried out in microtitration plates using 8 HAUs per well, according to standard procedures. Monoclonal antibody AVS-1 has been shown previously by Srinivasappa et al. in Avian Diseases 30: 562–567, 1986, to react specifically and extensively in the HI test with commercial Hitchner B 1 and LaSota strain vaccines.

TABLE 4

HI tests

| Antibody: | HI titre against: | | | |
|---|---|---|---|---|
| | CaTs | Hitchner B1 | C2 | NDW |
| AVS-1 (monoclonal) | <4; <4* | 7; 7 | 7; 7 | <4; 6 |
| Positive (polyclonal) | 9; 9 | 9; 9 | 9; 9 | 9; 9 |
| Negative serum | <4; <4 | <4; <4 | <4; <4 | <4; <4 |

*The results represent replicate tests and are expressed as $\log_2$

From the results of table 3 and table 4, the conclusion can be drawn that the NDV C2 strain has other properties than the CaTs, the Hitchner B, and the NDW

EXAMPLE 3

Efficacy of NDV C2 vaccine

NDV C2 virus was diluted to contain approximately 3–4 logs $EID_{50}$ of virus per 0.1 ml and was inoculated into 200 10–12 day-old SPF embryos. Embryos were placed at 37° C. Four days post-inoculation the embryos were candled and all live embryos were placed at 4° C. for 2 hours. Allantoic fluid was then harvested. A total 1340 ml of allantoic fluid was mixed with 660 ml of stabiliser. This was mixed for 15 minutes then filled into 10 ml glass vials, 2 ml per vial. The vials were then freeze-dried.

To establish the immunogenicity of the vaccine an eye drop (A) and spray immunisation (B) were carried out using one-day-old SPF chickens. See Table 5 and 7 for vaccination and challenge protocol. The virulent NDV strain Texas-GB was used for challenge 28 days after vaccination. All chickens were observed for signs of NDV infection for 14 days post-challenge. Such signs included nervous tremors, paralysis or death. Any chicken exhibiting one or more of these signs was considered not protected.

A. Efficacy of eye drop vaccination

TABLE 5

Vaccination and challenge protocol.

| Group | No. of birds/group | Vaccine | Route of inoculation | Vaccine titre/dose | Challenge titre/dose | Route of inoculation |
|---|---|---|---|---|---|---|
| A | 22 | NDV-C2 | i.o. | $10^{3.5}$ $EID_{50}$ | $10^{3.8}$ $EID_{50}$ | i.m. |
| B | 22 | NDV-C2 | i.o. | $10^{3.5}$ $EID_{50}$ | $10^{4.0}$ $EID_{50}$ | i.o. |
| C | 12 | none | — | — | $10^{3.8}$ $EID_{50}$ | i.m. |
| D | 12 | none | — | — | $10^{4.0}$ $EID_{50}$ | i.o. |

TABLE 6

Challenge results.

| Group | Vaccine | Challenge | Protection #Pos/Total | Percent |
|---|---|---|---|---|
| A | NDV-C2 | Texas-GB | 0/22 | 100 |
| B | NDV-C2 | Texas-GB | 0/22 | 100 |
| C | none | Texas-GB | 12/12 | 0 |
| D | none | Texas GB | 12/12 | 0 |

B. Efficacy of spray vaccination

TABLE 7

Vaccination and challenge protocol.

| Group | No. of birds/group | Vaccine | Vaccine titre/dose | Challenge titre/dose |
|---|---|---|---|---|
| A | 32 | NDV-C2 | $10^{4.2}$ EID$_{50}$ | $10^{4.9}$ EID$_{50}$ |
| B | 16 | none | — | $10^{4.9}$ EID$_{50}$ |

TABLE 8

Challenge results.

| Group | Vaccine | Challenge | Protection #Pos/Total | Percent |
|---|---|---|---|---|
| A | NDV-C2 | Texas-GB | 1/32 | 96.9 |
| B | none | Texas-GB | 16/16 | 0 |

Of the NDV C2 vaccinated chickens none (eye drop vaccination) or only 1 of 32 chickens (spray vaccination) exhibited signs of Texas-GB infection. All of the non-vaccinated control chickens exhibited signs of Texas-GB infection.

I claim:

1. A virus having all of the indentifying characteristics of the NDV C2 strain deposited at the CNCM of the Institute Pasteur, Paris, France under accession No. I-1614.

2. A vaccine for use in the protection of poultry against Newcastle Disease (ND) comprising a virus of the NDV C2 strain deposited at the CNCM of the Institute Pasteur, Paris, France under accession No. I-1614, and a pharmaceutical acceptable carrier or diluent.

3. A vaccine according to claim 2, wherein the virus is in a live form.

4. A vaccine according to claim 2, wherein the vaccine comprises $10^{3.0}$–$10^{8.0}$ EID$_{50}$, per animal.

5. A vaccine according to claim 2, further comprising a vaccine derived from one or more other pathogens infectious to poultry.

6. A vaccine according to claim 5, wherein the other pathogen is selected from the group consisting of IBV, IBDV, CAA virus and reovirus.

7. A method for the propagation of viruses according to claim 1 comprising the steps of:
   a. inoculating a susceptible substrate with the virus,
   b. allowing the MDV virus to multiply, and
   c. harvesting the NDV containing material.

8. A method for the preparation of a vaccine for use in the protection of poultry against ND, comprising combining the harvested NDV material obtained by the method according to claim 7 with a pharmaceutical acceptable carrier or diluent.

9. A method for controlling Newcastle Disease in poultry comprising administering an effective amount of the vaccine according to claim 2 to birds.

* * * * *

UNITED STATES PATENT AND TRADEMARK OFFICE
CERTIFICATE OF CORRECTION

PATENT NO.   : 5,750,111
DATED        : May 12, 1998
INVENTOR(S)  : Carla C. Schrier It is certified that error appears in the above-identified patent and that said Letters Patent is hereby corrected as shown below:

Column 10, line 25, claim 7, delete "MDV" and replace with -- NDV --.

Signed and Sealed this

Twenty-fifth Day of August, 1998

Attest:

BRUCE LEHMAN

Attesting Officer    Commissioner of Patents and Trademarks